United States Patent [19]

Loveless et al.

[11] Patent Number: 4,911,731
[45] Date of Patent: Mar. 27, 1990

[54] PROCESS AND COMPOSITION FOR DYEING HAIR UTILIZING AN ANIONIC POLYMERIC/CATIONIC POLYMER COMPLEX

[75] Inventors: Norman P. Loveless, Bethel; Leszek J. Wolfram, Stamford; Keith C. Brown, New Canaan, all of Conn.

[73] Assignee: Clairol Incorporated, New York, N.Y.

[21] Appl. No.: 938,332

[22] Filed: Dec. 3, 1986

Related U.S. Application Data

[63] Continuation of Ser. No. 681,718, Dec. 13, 1984, abandoned, which is a continuation of Ser. No. 468,733, Feb. 22, 1983, abandoned.

[51] Int. Cl.$^4$ .................................................. A61K 7/13
[52] U.S. Cl. ........................................... 8/405; 8/406; 8/426; 8/429
[58] Field of Search ..................... 8/405, 406, 426, 429

[56] References Cited

U.S. PATENT DOCUMENTS

| | | | |
|---|---|---|---|
| 4,182,612 | 1/1980 | Sokol et al. | 8/426 |
| 4,228,258 | 10/1980 | Sugio et al. | 525/390 |
| 4,240,450 | 12/1980 | Grollier et al. | 8/406 |
| 4,314,808 | 2/1982 | Jacquet et al. | 8/406 |
| 4,339,237 | 7/1982 | Wang et al. | 8/405 |
| 4,445,521 | 5/1984 | Grollier et al. | 8/406 |

Primary Examiner—John Kight
Assistant Examiner—Nathan M. Nutter
Attorney, Agent, or Firm—Charles J. Zeller

[57] ABSTRACT

A process and composition for dyeing hair involving the precipitation of an anionic polymeric dye by means of a cationic polymer preferably in the presence of a surfactant and particularly an amphoteric surfactant.

15 Claims, No Drawings

PROCESS AND COMPOSITION FOR DYEING HAIR UTILIZING AN ANIONIC POLYMERIC/CATIONIC POLYMER COMPLEX

This is a continuing application of application Ser. No. 681,718 filed Dec. 13, 1984, now abandoned, which is a continuation of application Ser. No. 468,733, filed Feb. 22, 1983, now abandoned.

This invention relates to a method for dyeing hair and to compositions that are useful for this purpose. More particularly, it concerns a method and composition for dyeing hair that makes use of high molecular weight polymeric anionic dyes which by virtue of their high molecular weight, greatly minimizes the possibility that the products containing such dyes will exhibit mutagenic, carcinogenic or teratogenic effects in humans.

The use of cationic polymer dye compounds for dyeing human hair has been suggested in the prior art. Typical teachings of this kind can be found in the U.S. Patents to Sokol et al 4,182,612; Jacquet et al 4,314,808 and Kalopissis et al 4,228,258. Sokol et al further suggest that their cationic polymeric dye compounds may be complexed with anionic polymers or anionic surfactants to form waxy materials. Although these may be used to produce colors, the patentees disclose that these colors have less substantivity than the cationic polymeric dyes and are accordingly more likely to rub off or wash off.

It is often desirable to employ anionic polymeric dyes (hereinafter referred to as anionic polydyes) to develop certain colors in hair. However, solutions of these anionic polydyes form films on evaporation that are brittle and which are soluble in water. Because of these characteristics, they are readily removed by abrasion or rinsing with water and accordingly, are not suitable by themselves for hair dyeing applications. However, it has been found that when mixed with certain water soluble cationic polymers, the anionic polydyes form ionic complex precipitates which are insoluble in water. These complexes in addition are substantive to hair and not readily removed with water.

It is accordingly an object of the present invention to provide a process and composition for dyeing hair using dye materials that are anionic polydye dye/cationic polymeric complexes of high molecular weight and which consequently have a low potential for exhibiting mutagenic, carcinogenic or teratogenic effects in humans.

It is also an object of the present invention to provide a process and product described in the above object which gives a substantive hair dyeing and cannot be readily removed by water.

It has also been found in line with the present invention that the use of certain surfactants in the aforementioned system gives superior dyeing results. These materials provide surface activity to the system (thus levelling the color) and enables the polymeric anionic dye/cationic polymer complex to be precipitated quantitatively.

It is accordingly a further object of the present invention to provide a process for dyeing hair involving the precipitation of a polymeric anionic dye by certain cationic polymers in the presence of certain surfactants.

Other and more detailed objects of this invention will be apparent from the following description and claims.

The invention relates to a process for dyeing hair, in which there is applied to the hair for a time sufficient to dye said hair, a dye bath containing an effective dyeing amount of at least an anionic polymeric dye and a cationic polymeric compound; the cationic polymeric compound being capable of precipitating said anionic polymeric dye on the hair as a complex containing the anionic polymeric dye and the cationic polymer; the anionic polymer dye and said cationic polymer being present in the dye bath at concentrations which will cause the precipitate to be deposited on the hair as fine particles which form a film that adheres to the hair.

The dye bath can also contain a surfactant to insure the essentially complete precipitation of the complex.

The components of the dye bath can be present therein at levels within the following ranges:

|   |   | % by Wt. based on Total Wt. of dye bath |
|---|---|---|
| (1) | Anionic polymeric dye | from about 0.1% to about 0.2% |
| (2) | cationic polymer | from about 0.5% to about 1.0% |
| (3) | surfactant | about 1.0% |

Suitably: (a) the anionic polymeric dye is of the formula:

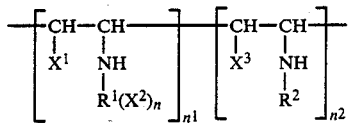

in which:
 (1) $R^1$ is a chromophore;
 (2) $X^1$, $X^2$ and $X^3$ are H or an anionic group at least one of $X^1$, $X^2$ or $X^3$ being an anionic group;
 (3) $R^2$ is H, acyl or the group $-R^1(X^2)_n$;
 (4) n is 0 or 1; and
 (5) $n^1$ and $n^2$ are numbers designating the degree of polymerization,
(b) said cationic polymer is of the formula:

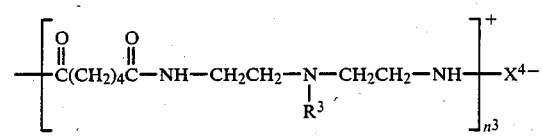

wherein:
 (1) $R^3$ is alkyl or substituted alkyl;
 (2) $X^{4-}$ is an anionic group; and
 (3) $n^3$ is a number designating the degree of polymerization, and
(c) said surfactant is an amphoteric surfactant.

Suitably: (a) the chromophore $R^1$ can be a nitrobenzene, anthrapyridine, anthraquinone, azo dye, nitroaniline, xanthene dye, benzanthrone dye or a naphthalimide dye; the group $R^3$ of the cationic polymer is epoxypropyl or dimethylaminohydroxypropyl; further; said surfactant is coco imidazoline; $X^2$ is an anionic group; and n is 1.

Advantageously, the dye bath is formed just prior to applying it to the hair by mixing a liquid dye composition comprising said anionic polymeric dye in a liquid vehicle with a liquid polymeric composition comprising said cationic polymer in a liquid vehicle. The liquid dye composition suitably contains a plurality of anionic polymeric dyes.

The invention further involves a composition for dyeing hair, involving a dye bath containing an effective dyeing amount of at least an anionic polymeric dye and a cationic polymeric compound; the cationic polymeric compound being capable of precipitating the anionic polymeric dye as a complex containing the anionic polymeric dye and the cationic polymer on hair when the composition is applied to hair; the anionic polymeric dye and the cationic polymer being present in the dye bath at concentrations which will cause the precipitate to be deposited on the hair as fine particles which form a film that adheres to hair when the composition is applied to hair.

Suitably the composition includes a surfactant which insures the essentially complete precipitation of the complex. Advantageous by the anionic polymeric dye is of the formula:

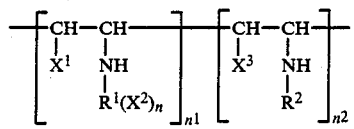

in which:
(1) $R^1$ is a chromophore;
(2) $X^1$, $X^2$ and $X^3$ are H or an anionic group at least one of $X^1$, $X^2$ or $X^3$ being an anionic group;
(3) $R^2$ is H, acyl or the group $-R^1(X^2)_n$;
(4) n is 0 or 1; and
(5) $n^1$ and $n^2$ are numbers designating the degree of polymerization, the cationic polymer is of the formula:

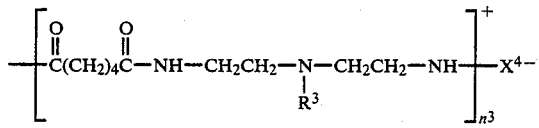

wherein:
(1) $R^3$ is alkyl or substituted alkyl;
(2) $X^{4-}$ is an anionic group; and
(3) $n^3$ is a number designating the degree of polymerization; and the surfactant is an amphoteric surfactant. Suitably $X^2$ is an anionic group and n is 1.

Most suitably the composition is a two part hair dyeing composition in which the first part is a liquid dye composition and the second part is a liquid polymeric composition; the first and second parts being adapted to be mixed together just before use to form a dye bath; the liquid dye composition is suitably a liquid vehicle having distributed therein at least one anionic polymeric dye; the liquid polymeric composition is suitably a liquid vehicle having distributed therein a cationic polymer compound; the cationic polymeric compound being capable of precipitating the anionic polymeric dye on hair as a complex containing the anionic polymeric dye and said cationic polymer when the dye bath is applied to hair; the anionic polymer dye and the cationic polymer being present in the dye bath when it is formed at concentrations which will cause the precipitate to be deposited on the hair as fine particles which form a film that adheres to the hair.

In the two part composition the liquid dye composition suitably also contains a surfactant which insures the essentially complete precipitation of the complex.

Advantageously in the two part composition the anionic polymeric dye is of the formula:

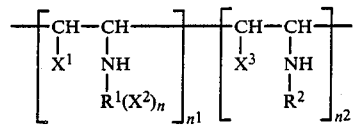

in which:
(1) $R^1$ is a chromophore;
(2) $X^1$, $X^2$ and $X^3$ are H or an anionic group at least one of $X^1$, $X^2$ or $X^3$ being an anionic group;
(3) $R^2$ is H, acyl or the group $-R^1(X^2)_n$;
(4) n is 0 or 1; and
(5) $n^1$ and $n^2$ are numbers designating the degree of polymerization;
the cationic polymer is of the formula:

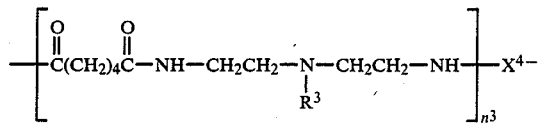

wherein:
(1) $R^3$ is alkyl or substituted alkyl;
(2) $X^{4-}$ is an anionic group; and
(3) $n^3$ is a number designating the degree of polymerization; and
the surfactant is an amphoteric surfactant.

In the two part composition $X^2$ is advantageously an anionic group, and n is 1.

The anionic polydyes used in the present invention are generally characterized as colorless polymeric backbones to which are attached monomeric chromophores. In addition, these anionic polydyes in solution contain anionic groups (e.g.

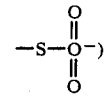

that may be bonded to the polymeric backbione, the chromophore or both. In a preferred form of this invention, the colorless backbone of the anionic polydye comprises poly(aminoethylene) or its copolymers. These backbones are prepared by the homopolymerization of vinyl amine or the copolymerization of the vinyl amine with other polymerizable monomers.

In some instances, it has been found to be advantageous to acetylate at least to some degree the free amino groups present on the backbone of the poly(aminoethylene). This precludes the protonation of these amino groups thus enhancing the water solubility of the anionic polydye. This is especially important when there is a high degree (>50%) of chromophore substitution on the polymeric backbone.

The class of anionic polydyes that are especially useful in the practice of the present invention may be described by the general formula:

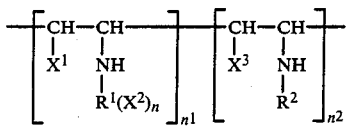
(I)

in which:
(a) $R^1$ is a chromophore;
(b) $X^1$, $X^2$ and $X^3$ are H or an anionic group, at least one of $X^1$, $X^2$ or $X^3$ being an anionic group;
(c) $R^2$ is H, acyl or the group $-R^1(X^2)_n$;
(d) n is 0 or 1 and preferably 1; and
(e) $n^1$ and $n^2$ are numbers designating the degree of polymerization.

The molecular weight of the anionic polydyes used in this invention may vary over a relatively wide range. Ordinarily, however, this will fall within the range of from about $10^3$ to about $1 \times 10^8$ with the preferred range being from about $10^3$ to about $6 \times 10^5$.

The degree of chromophore substitution in the anionic polydyes employed in this invention may also vary. This can be quantitatively expressed as the mer % which designates the fraction of amino groups on the polymeric backbone to which the chromophore is attached. Generally, this mer % will be in the range of from about 10% to about 95%, with the preferred range being from about 20% to about 70%.

The anionic groups (e.g. $X^1$, $X^2$ and $X^3$) contained in the anionic polydyes employed in the present invention may all be the same or they may be different from each other and may be any of a variety of anionic groups. By way of illustrating these anionic groups, mention may be made of carboxyl, phenolic, phosphate and phosphoric. In the preferred cases, however, this will be the sulfonate group i.e.

The degree of anionic substitution of the anionic polydyes utilized in this invention may vary over a range. As noted above, this substitution might be on the backbone of the polymer chain on the chromophore or on both. This degree of substitution can be expressed as that percentage of repeating units which carry a negative charge. In general, this will fall within the range of from 10% to about 95% and preferably, in the range of from about 20% to about 70%.

As also noted above, it is sometimes advantageous to acylate at least to some degree the free amino groups on the polymeric backbone of the anionic polydye used in the present invention. The degree of acylation may also vary over a wide range. This degree of acylation can be expressed as that percentage of backbone amino groups which are acetylated. Usually, this will vary from about 0 to about 95% and preferably from about 30% to about 80%.

The form of the anionic polydye shown in Formula I above will be the form of the polydye when it is in its ionic form in solution. In preparing the liquid composition which will contain the anionic polydye, this dye will usually be added to the liquid in the form of a salt of the anionic polydye and particularly, the alkali metal salt (e.g. sodium salt). The salt is formed between the anion of the anionic polydye and the alkali metal.

It is also within the scope of the present invention to prepare the liquid composition containing the anionic polydye by adding it to the liquid carrier in the form of an amphoteric polydye. These differ from the anionic polydyes only in that the free amino groups on the backbone have not been acylated after the chromophore has been coupled with the polymeric backbone. However, these amphoteric polydyes have a pH of above 9 in solution and therefore, behave as anionic polydyes in solution.

The chromophore (e.g. $R^1$ in formula I) can be any of a variety of color forming groups. Illustrative of the chromophore types that may be contained in the anionic polydye employed herein, mention may be made iof nitrobenzenes, anthrapyridines, anthraquinones, azo dyes, nitroaniline, xanthene, phthalocyanine, benzanthrone, triarylmethane, and naphthalimide dyes.

A number of anionic polydyes that can be used in this invention are described in the prior art (see U.S. Pat. Nos. 4,144,252 to Wang, et al., 4,233,328 to Dawson, et al. and 4,206,240 and 4,182,885 both to Bunes) and are available in the trade. The structures of some that have been found to be particularly useful are given in Table I below. In addition, the structure of an orange polydye (Dye O') having an azo dye chromophore is also given in this Table.

TABLE I

Structures of Anionic Polydyes

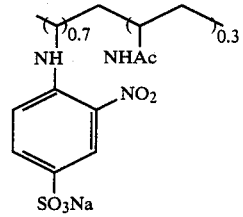

Dye Y

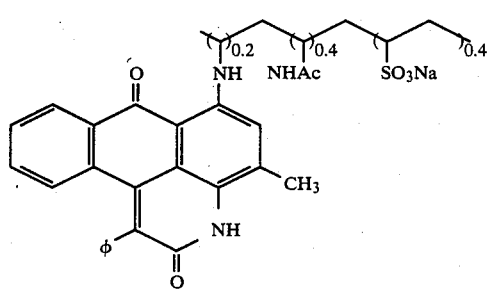

Dye R

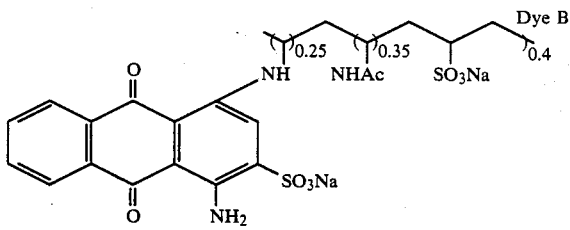

Dye B

TABLE I-continued
Structures of Anionic Polydyes

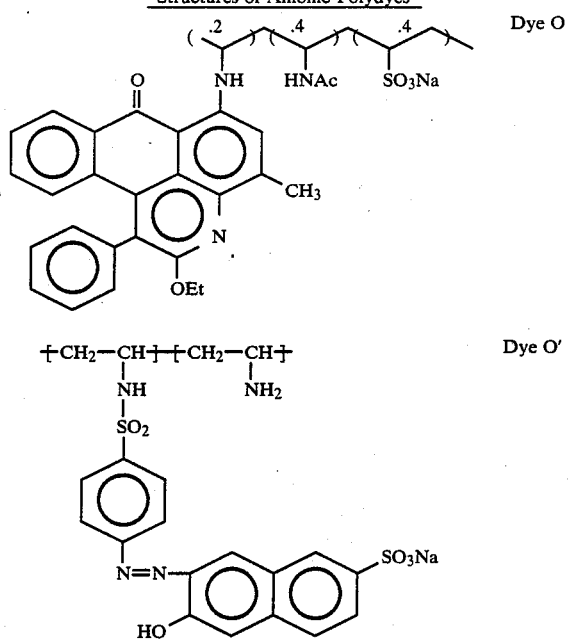

Average m wt. 20,000 to 40,000.

Some of the further chemical properties of some of the anionic polydyes shown in Table I are given below in Table II.

TABLE II
Chemical Properties of Polydyes

| Poly-Dye | Chromophore type | C-Mer %* | AC-Mer %** | SO₃-Mer %*** | Mol. Wt. Range | Mp$^{PSS}$ |
|---|---|---|---|---|---|---|
| Dye Y | Nitrobenzene | 70 | 30 | — | $10^3$–$6 \times 10^5$ | $10^5$ |
| Dye R | Anthrapyridine | 20 | 40 | 40 | $10^3$–$5 \times 10^5$ | $4.5 \times 10^4$ |
| Dye B | Anthraquinone | 25 | 35 | 40 | $10^3$–$5 \times 10^5$ | $4.5 \times 10^4$ |
| Dye O | Anthrapyridine | 20 | 40 | 40 | $10^3$–$6 \times 10^5$ | $4.5 \times 10^4$ |

*C-Mer % = fraction of free amino groups to which chromophore is attached
**AC-Mer % = fraction of free amino groups acetylated
***SO₃-Mer % = fraction of free amino groups replaced with —SO₃Na
Mp$^{PSS}$ = peak molecular weight relative to poly(styrene sulfonate)
Note:
Mer % given approximately It is within the scope of the present invention to use the aforesaid anionic polydyes either singly or in combination with each other. To obtain more natural looking shades (e.g. brown, black, auburn, platinum) the primary color polydyes (e.g. Dye Y, Dye R, Dye B, Dye O) are mixed in the appropriate proportions to give the desired shade. These will be simultaneously precipitated on the hair by means of one or more cationic polymers as described above.

As indicated above, a feature of the present invention involves the precipitation of the anionic polydye onto the hair by means of certain cationic polymers as a polydye/cationic polymer complex. It has been found that the physical properties of the precipitated polydye complex influences the ability of the complex to properly dye hair. It has also been found that the nature of this precipitation is, among other things, a function of the concentration of the anionic polydye in the treating solution. Optimally, the goal is to control the rate of precipitation so that the anionic polydye/cationic polymer complex is laid down as a smooth film.

The concentration of the anionic polydye that can be employed in the present invention may vary somewhat. Usually, at concentrations above about 0.2%, the precipitation of anionic dye/cationic complex is rapid resulting in large agglomerates of dye complex which may not be commercially acceptable for dyeing hair. Therefore, in the usual practice of this invention, the anionic polydye concentration employed will rarely exceed about 0.2% by weight based on the total weight anionic polydye composition. The lower limit of anionic polydye concentration is limited only by the degree of dye take on the hair which is commercially acceptable. This in practice has been found to be about 0.1%. In the preferred form of this invention, however, the concentration of anionic polydye employed will be about 0.15% by weight based on the total weight of anionic polydye composition.

In the practice of the process of the present invention, the anionic polydye will ordinarily be employed as a liquid dye composition in which the polydye is distributed in a liquid carrier. The liquid carrier may be a solvent for the polydye or simply a suspending medium. In the preferred form of this invention, the liquid carrier will serve as a solvent for the anionic polydye.

A variety of liquids may be employed as a carrier for the anionic polydyes utilized in this invention. By way of example, mention may be made of water, aqueous lower alkanols containing 2 to 4 carbon atoms e.g. ethyl alcohol, isopropyl alcohol. In the preferred practice of this invention, the liquid carrier will be water.

It has also been found that to insure essentially complete precipitation of the anionic polydye/cationic polymer complex, it is advantageous to have the precipitation take place in the presence of certain surfactants. In practice, the surfactant usually will be part of the liquid dye composition which will eventually be mixed with a cationic polymer liquid composition in a manner described in more detail below to precipitate the polydye/polymer complex on the hair.

A variety of selective surfactants may be employed for the purposes of the present invention. Among those that may be mentioned are the phosphate esters, sulfated fatty oils, amphoteric surfactants. By way of specific exemplification of the surfactant that can be used herein are Amphoteric-1 (e.g. Amphoterge K-2); sulfonated tall oil fatty acids (e.g. Actrasol SP); phosphated high molecular weight alcohol (e.g. Emkatex-Dx);

phosphate ester (e.g. Hipochem FS) etc. (See McCutcheon's "Emulsifiers and Detergents", North American Editions 1979 and 1981).

One surfactant that has been found to be particularly useful is Amphoteric-1 (CTFA nomenclature RD Number 977055-98-3 CTFA Cosmetic Ingredient Dictionary, Second Edition, 1977, p. 24). This is a coco imidazoline and is represented by the formula:

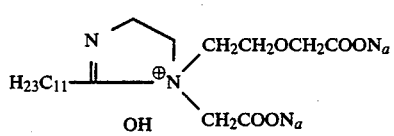 (II)

This surfactant is available commercially from a number of manufacturers. One suitable source is the product Amphoterge K from Lonza Inc.

The use of Amphoteric-1 has several special advantages. Not only does it assist quantitative precipitation of the polydye/cationic polymer complex, but it allows the complex to coat the hair more uniformly. Moreover, this does not impart a greasy feel to the hair as do some iother surfactants.

The quantity of surfactant that will be contained in the liquid dye composition of this invention may also vary over a range. Usually, this will constitute between about 0.5% to about 5% by weight based on the total weight of the liquid dye composition and preferably from about 1.0% to about 2.0% on the same weight basis.

The cationic polymers that can be used in accordance with the present invention are quite selective. Generally, these cationic polymers are adipic acid/N-substituted diethylenetriamine copolymers. These conform generally to the formula:

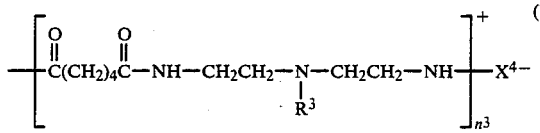 (III)

wherein $R^3$ is alkyl or substituted alkyl; $X^4$ is an anionic group e.g. halogen and particularly Cl; $n^3$ is a number designating the degree of polymerization. By way of illustration $R^3$ may be epoxypropyl, dimethylaminohydroxypropyl, etc. The molecular weight of these cationic polymers may vary over a relatively wide range.

The cationic polymers that have been found to be especially useful for the purposes of this invention are available under the trade designation Delsette 101 (Hercules) and Cartaretin F-4 (Sandoz). Delsette 101 is adipic acid/epoxypropyl diethylenetriamine copolymer (CTFA Dictionary designation RD Number 977062-97-7) and conforms generally to formula III above where $R^3$ is epoxypropyl and $X^4$ is Cl. Cartaretin F-4 is adipic acid/dimethylaminohydroxypropyl diethylenetriamine copolymer (CTFA Dictionary designation) and corresponds to formula III above in which $R^3$ is dimethylaminohydroxypropyl and $X^4$ is Cl.

As in the case with the anionic polydye, the cationic polymer will usually be employed in the form of a cationic polymer liquid composition in which the cationic polymer is distributed in a liquid carrier. The liquid carrier may serve as a solvent for the cationic polymer or as a simple suspending medium. However, in the usualcase, the liquid carrier will serve as a solvent.

A variety of liquid carriers may be employed as a vehicle for the cationic polymer. By way of example, water and aqueous alkanols may be mentioned. In the preferred form of the invention, the liquid carrier will be water.

The concentration of the cationic polymer that may be used in this invention may vary somewhat. This will ordinarily be related to the concentration of the polydye in the liquid dye compositions. The cationic polymer will, for the most part, be used in sufficient concentration to precipitate all of the anionic polydye contained in the liquid dye composition. Generally, however, this concentration will fall within the range of from about 0.5% to about 5.0% by weight based on the total weight of the cationic polymer liquid composition, the preferred concentration range being from about 1.0% to about 2.0% on the same weight basis.

The selectivity of the cationic polymers that are useful for the purposes of the present invention can be gleaned from the study summarized in Table III below. In this study a variety of cationic polymers used in the same vehicle and at the same concentration (0.5%) was mixed under the same conditions with the anionic polydye solution at the same concentration (0.1%). The characteristics of the polydye/cationic polymer complex formed and the ability of such precipitate to form film on hair and therefore, to be useful in coloring hair was observed.

TABLE III

Characteristics of Polydye/Cationic Polymer Complexes*

| Cationic Polymer | Description of Precipitate | Forms a Film on Hair? |
| --- | --- | --- |
| Merquat 100 | Oily gel, no exhaustion | No |
| Onamer M | Oily gel, no exhaustion | No |
| Celquat H 60 | Oily gel | No |
| Celquat L 200 | Oily gel | No |
| Cartaretin F-4 | Ultrafine particles, viscid | Yes |
| Polymer JR | Oily gel | No |
| Delsette 101 | Ultrafine particles, viscid | Yes |
| Delsette 201 | Large particles | No |
| Gafquat 755 B | Oily liquid, no exhaustion | No |
| Gafquat 755A | Viscous, elastic gel | No |
| Merquat,550 | Viscous, elastic gel | No |

*20 ml of bath: 0.1% polydye 0.5% cationic polymer

It will be noted that only in the cases of Delsette 101 and Cartaretin F-4 were fine particle precipitates formed. Furthermore, it was only in these cases in which films of the precipitate were formed on the hair.

In reviewing the differences between the structural characteristics of the cationic polymers listed in Table III, it is noted that the cationic polymers which did not form a film on hair are all of the type that is intrinsically cationic, i.e. have an intrinsic positive charge associated with them. That positive charge remains on the polymeric moiety irrespective of pH and/or interaction with other ionic materials. On the other hand Cartaretin F-4 (CTFA name: adipic acid/dimethylaminohydroxypropyl diethylenetriamine copolymer) and Delsette 101 (CTFA name: adipic acid/epoxypropyl diethylenetriamine copolymer), have no intrinsic positive charge associated with them. These polymers contain, however, basic moieties in the form of secondary and tertiary nitrogen atoms which under certain conditions (pH, interaction with strongly acid groups, etc.) can develop positive charges and thus become cationic. Such polymers, which have no intrinsic positive charge but which can acquire an intrinsic positive charge, have been found to be suitable for use in accordance with the present invention. "Conventional" cationic polymers—those having an intrinsic positive charge—have been shown above to be unsuitable.

Without intending to be bound by the following theory, the selective utility of polymers such as Cartaretin F-4 and Delsette 101 might be explained by the rate of complex formation which takes place in accordance with the present invention. The coulombic (electrostatic) interactions between charged materials are usually very fast, even those which involve polymers. Such fast interactiions are undesirable in connection with hair coloring. When an anionic polydye is mixed with a regular cationic polymer, i.e. one that has a permanent positive charge associated with it, there is an almost instantaneous creation of a polymer-polymer complex which forms a heavy and copious precipitate that is useless for aesthetic hair coloration. On the other hand, a combination of an anionic polydye with a polymer in accordance with the present invention leads to a slow complex formation apparently reflecting the gradual buildup of cationic charges. The precipitate forms a very fine suspension of particles having strong affinity to hair surface.

In carrying out the process of the present invention, a dye bath is usually first formed by mixing predetermined volumes of the liquid dye compositions and the liquid cationic polymer composition. The relative volumes of the respective liquid composition employed are such that equivalent amounts of anionic polydye and cationic polymer are present in the dye bath. Usually, the concentrations are adjusted so that equal volumes of liquid dye composition and liquid polymeric compositions are employed.

The total volume of the dye bath utilized will depend on the weight of the hair to be treated. Acceptable coloring is obtained with at least 10 ml of dye bath per 2 grams of hair. With this quantity of dye bath, there is applied a $0.55\mu$ coating of complex (of which 16.5% is contributed by the polydye). With higher ratios of dye bath volume to hair weight, hair dyeings of deeper intensity are obtained.

In practicing the process of the present invention, the dye bath is prepared just prior to applying it to the hair by mixing the anionic polydye liquid composition with the cationic polymer liquid composition. The dye bath so formed is then applied to the hair for a short period of time (e.g. from about 10 sec. to about 5 min.) at ambient temperatures and then the hair is rinsed and dried.

The quantities of anionic polydye, surfactant and cationic polymer that may be contained in the dye bath may vary somewhat. Table IV below gives the general range and the preferred range of these agents in the dye bath.

TABLE IV

| | % by Weight in Dye Bath | |
|---|---|---|
| | General | Preffered |
| Polydye | 0.1 to 0.2 | .1 |
| Surfactant | 0 to 10 | .5 |
| Cationic polymer | 0.5 to 1.0 | .5 |

In accordance with the present invention, the polydye/cationic polymer/surfactant precipitates from solution as ultrafine particles in a viscid matrix, which remains somewhat sticky until fully dried. When applied to hair, this tacky film causes hair fibers to stick together and makes combing more difficult. After drying, the hair is no longer tacky, but still feels somewhat coated, and is more difficult to comb than untreated hair.

The "water bleed" of hair dyed in accordance with the process of the present invention is zero even after successive rinsings. That is to say that no color is leached from the dyed hair by water even with successive rinsings with water. Moreover, these dyeings are relatively stable to light; there being no light fading even after exposure in the Fadeometer for 10 hours. It was only after storage over a long period of time (6 months) that fading was noted.

The anionic polydye/cationic polymer/surfactant systems of this invention impart temporary color to the hair. That is to say that the coatings may be removed by shampoo. However, the degree of resistance to shampooing varies not only with the particular cationic polymer employed, but also is dependent on the cosmetic history of the hair etc. Thus, for example, in the case of Cartaretin F-4 the coating may be removed with two latherings. When Delsette 101 is used, a more substantive complex is formed requiring four or five latherings for removal. The degree of substantivity of the colored polydye complex to hair depends on the physical condition of the hair prior to dyeing. The extent of damage to the hair before dyeing markedly influences the shampoo removability of the dye complex. The Table below gives examples of the effect of several pretreatments on shampoo removal. Pretreatment with hydrogen peroxide (adjusted to pH 9) for eight minutes prior to polydyeing significantly increases the adhesion of the polydye complex. Persulfate bleaching of the hair makes the polydye coating essentially permanent.

These results correlate well with Rubine dye tests on the same tresses. They show that Delsette has much greater substantivity for damaged hair than for virgin hair.

TABLE V

| Substantivity of Polydyes to Damaged Hair | | |
|---|---|---|
| Pretreatment | Time on Hair (Minutes) | Number of Shampoos Required to Remove Color |
| No pretreatment (Polydye complex on virgin hair) | 1–3 | 2 |
| Oxidation dye base with peroxide | 20 | 3 |
| Peroxide alone | 8 | 3 |
| Peroxide alone | 20 | 3 |
| 0.8% Monoethanolamine | 20 | 5 |
| Persulfate/Peroxide Bleach | 60 | >10 |

It is also within the purview of the present invention to repetitively color hair with the polydye/cationic polymer systems of the present invention to obtain darker shades. With these repetitive dyeings, it has been found advantageous to shampoo the hair after each dyeing cycle in order to reduce any negative effect on the cosmetic properties of the hair.

It may sometimes be desirable to provide the hair dyed with the present system with an overcoat. This will usually be done after the hair has been dyed. Water soluble resins may be used for this purpose or polymers such as polyvinyl alcohol (e.g. Elvanol) or Polyox resins cross linked with a variety of insolubilizers.

In some instances, it may be advantageous to add a precipitation inhibitor to the system to regulate the nature of the precipitate that will be laid down on the hair. As previously pointed out at certain concentrations of polydye, the rate of precipitation is too fast resulting in the deposition of large aggregates of complex which do not properly dye hair. By using some precipitation inhibitors, it may be possible to use higher concentrations of polydye to get deeper dyeings and yet not produce large particulate precipitations. A number of materials have been found which serve as precipitation inhibitors. These include polar organic solvents, cosmetic thickening agents, anionic-, cationic-, or nonionic surfactants. By way of exemplifying agents that may serve as precipitation inhibitors, the following may be mentioned: cellosolve ethers (me, Bu), dimethylformamide, dimethylsulfoxide, ethanol (>40%),, isopropanol, glycerol, ethylene glycol, Methocels, Carbopols, Polyox, tetraethylammonium chloride, trimethylbenzylammonium chloride, dimethyldihydroxyethylammonium chloride, Gafquat A, Natrosols, Tergitol (alkylphenol ethoxylates), sodium lauryl ether sulfate (>0.2%).

In some instances, it may be desirable to increase the rate at which the polydye complex is exhausted from the dye bath. This could increase the depth of dyeing that is obtained with a given dye bath. A number of materials are known in the prior art which can be used for this purpose. Most of these materials are cationic. The following are examples of materials that can be used for this purpose: Merquat 100, Merquat 500, Catrex, Cartaretin, Dupont Zonyl fluoro surfactants, Silicone polymers (Dow Corning), Dimethyldibenzylammonium chloride, Dimethyldidodecylammonium chloride, Stearyldimethylbenzylammonium chloride, Quaternized polyvinyl pyridine (30–100% quaternized).

The liquid dye composition and/or the liquid cationic polymer system used in the process of this invention may be preserved with conventional preservatives. These include such things as methyl and propyl paraben, DMDMH (1,3-dimethylol-5,5-dimethyl hydantoin), 2-phenoxyethyl, quaternium-15 (CTFA nomenclature) or combinations thereof. One preservative system that has been found particularly useful for the anionic polydye liquid composition consists of 0.1% quaternium-15 (Dowicel 200), 0.1% methyl paraben and 0.02% propyl paraben. A suitable preservative system for the cationic polymer liquid composition consists of 0.1% 2-phenoxyethanol, 0.1% methyl paraben and 0.02% propyl paraben.

The following Examples are given to further illustrate this invention. It is to be understood, however, that the invention is not limited thereto.

EXAMPLE 1

A. Cationic Polymeric Liquid Composition

| Ingredient | % by Weight |
| --- | --- |
| Delsette 101 | 8.0 |
| Propyl paraben | 0.02 |
| Methyl paraben | 0.1 |
| 2-Phenoxy ethanol | 0.1 |
| Water q.s. to | 100.00 |
| or | |
| Cartaretin F-4 | 3.33 |
| Propyl paraben | 0.02 |
| Methyl paraben | 0.1 |
| 2-Phenoxy ethanol | 0.1 |
| Water q.s. to | 100.00 |

B. Anionic Polydye Liquid Composition (Brown)

EXAMPLE 1-continued

| Ingredient | % by Weight |
| --- | --- |
| Dye B* | 0.0500 |
| Dye R* | 0.0300 |
| Dye Y* | 0.0800 |
| Dye O* | 0.0400 |
| Amphoterge K-2 | 2.5000 |
| Dowicil 200 | 0.1000 |
| Methyl paraben | 0.1000 |
| Propyl paraben | 0.0200 |
| Water q.s. to | 100.0000 |

EXAMPLE 2

A. Cationic Polymeric Liquid Composition
Same as Example 1
B. Anionic Polydye Liquid Composition (Black)

| Ingredient | % by Weight |
| --- | --- |
| Dye B | 0.0790 |
| Dye R | 0.0570 |
| Dye Y | 0.0630 |
| Dye O | 0.0110 |
| Amphoterge K-2 | 2.5000 |
| Dowicil 200 | 0.1000 |
| Methyl paraben | 0.1000 |
| Propyl paraben | 0.0200 |
| Water q.s. to | 100.0000 |

EXAMPLE 3

A. Cationic Polymer Liquid Composition
Same as Example 1
B. Anionic Polydye Liquid Compostition (Platinum)

| Ingredient | % by Weight |
| --- | --- |
| Dye B | 0.045 |
| Dye R | 0.004 |
| Dye Y | 0.001 |
| Amphoterge K-2 | 0.625 |
| Dowicil 200 | 0.100 |
| Methyl paraben | 0.100 |
| Propyl paraben | 0.020 |
| Water q.s. to | 100.000 |

It is obvious to those skilled in the art that many desired shades can be formulated by judicious combination of the dyes.

The compositions described in Examples 1 through 3 above were used to dye heads using the following procedure:

(1) shampoo the hair using 2 latherings and then rinse with water;
(2) mix Compositions A and B of each Example in equal volumes (125 ml each/250 ml total) to form the dye bath;
(3) apply dye bath to hair and let is remain in contact with hair for one minute;
(4) rinse hair thoroughly with water;
(5) optionally, apply conditioning agent (e.g. 1% SMALL MIRACLE solution); and
(6) rinse with water and dry.

Although the invention has been described with reference to specific forms thereof, it will be understood that many changes and modifications may be made without departing from the spirit of this invention.

What is claimed is:

1. A process for dyeing hair comprising applying to hair a dye composition containing (i) at least one anionic polydye of the formula

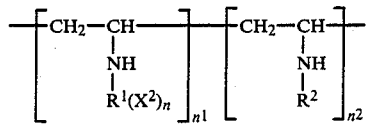

wherein $R^1$ is a chromophore; $R^2$ is H, acyl, or $-R^1(X^2)_n$; $X^2$ is an anionic group; n is 0 or 1, and $n^1$ and $n^2$ are numbers designating degree of polymerization, and (ii) a polymeric compound of the formula

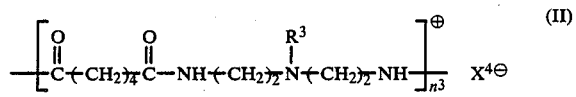

wherein $R^3$ is epoxypropyl or dimethylaminohydroxypropyl; $X^4$ is an anionic group, and $n^3$ is a number designating degree of polymerization, said anionic polydye (I) and said polymeric compound (II) each being present in said composition at concentrations effective to interactively form an amount of a water-insoluble polymeric complex sufficient to be deposited on the hair as an adhering film when the composition is applied to the hair, whereby the hair is dyed.

2. The process according to claim 1 wherein said dye composition also contains a surfactant which ensures the essentially complete precipitation of said complex.

3. The process according to claim 2 wherein the components of said dye composition are present in said dye composition at levels within the following ranges:

|  | % by Wt. Based on Total Wt. of Dye Composition |
| --- | --- |
| (1) Anionic poyldye (I) | from about 0.1 to about 0.2% |
| (2) Cationic polymer (II) | from about 0.5% to about 1.0% |
| (3) Surfactant | to about 1.0% |

4. The process according to claim 3 wherein the chromophore $R^1$ is selected from the group consisting of nitrobenzenes, anthrapyridines, anthraquinones, azo dyes, nitroanilines, xanthene, phthalocyanine, benzanthrone and naphthalimide dyes; the surfactant is an amphoteric surfactant, and n is 1.

5. The process according to claim 4 wherein said amphoteric surfactant is coco imidazoline.

6. The process according to claim 1 further comprising forming said dye composition just prior to its application to the hair by mixing a liquid dye vehicle containing said anionic polydye (I) with a liquid vehicle containing said polymer (II).

7. The process according to claim 6 wherein said liquid dye vehicle contains a plurality of anionic polydyes.

8. A composition for dyeing hair comprising (A) an effective hair dyeing amount of at least one anionic polydye of the formula

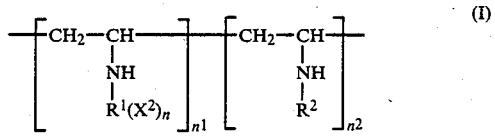

wherein $R^1$ is a chromophore; $R^2$ is H, acyl, or $-R^1(X^2)_n$; $X^2$ is an anionic group; n is 0 or 1, and $n^1$ and $n^2$ are numbers designating degree of polymerization, and (B) a polymeric compound of the formula

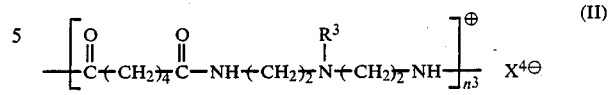

wherein $R^3$ is epoxypropyl or dimethylaminohydroxypropyl; $X^4$ is an anionic group, and $n^3$ is a number designating degree of polymerization, said anionic polydye (I) and said polymeric compound (II) each being present in said composition at concentrations effective to interactively form an amount of a water-insoluble polymeric complex sufficient to be deposited on the hair as an adhering film when the composition is applied to the hair, whereby the hair is dyed.

9. The composition according to claim 8 further comprising a surfactant which ensures the essentially complete precipitation of said complex.

10. The composition according to claim 9 wherein said surfactant is an amphoteric surfactant.

11. The composition according to claim 8 in which $X^2$ is an anionic group and n is 1.

12. A two-part composition for dyeing hair comprising as a first part a liquid vehicle including a dye and as a second part a liquid vehicle including a polymer, said first and said second parts being suitable for admixture just prior to use to form a hair dye composition, the dye in said first part being an anionic polydye of the formula

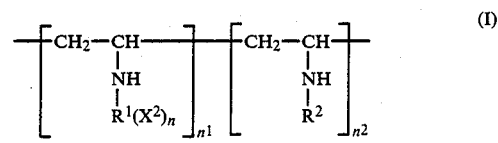

wherein $R^1$ is a chromophore; $R^2$ is H, acyl, or $-R^1(X^2)_n$; $X^2$ is an anionic group; n is 0 or 1, and $n^1$ and $n^2$ are numbers designating degree of polymerization and the polymer in said second part being a polymeric compound of the formula

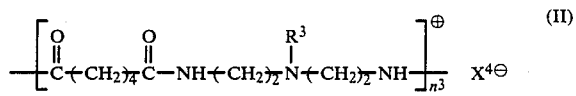

wherein $R^3$ is epoxypropyl or dimethylaminohydroxypropyl; $X^4$ is an anionic group, and $n^3$ is a number designating degree of polymerization, said anionic polydye (I) in said first part and said polymeric compound (II) in said second part, when admixed, being present in said hair dye composition at concentrations effective to interactively form an amount of a water-insoluble polymeric complex sufficient to be deposited on the hair as an adhering film when the composition is applied to the hair, whereby the hair is dyed.

13. The two-part composition according to claim 12 wherein said liquid dye vehicle also contains a surfactant which ensures the essentially complete precipitation of said complex in the hair dye composition.

14. The composition according to claim 12 wherein $X^2$ is an anionic group and n is 1.

15. The composition of claim 13 wherein said surfactant is an amphoteric surfactant.

* * * * *